(12) United States Patent
Sadler (10) Patent No.: US 8,535,426 B2
(45) Date of Patent: *Sep. 17, 2013

(54) APPARATUS, SYSTEM, AND METHOD FOR REMOVING ETHYLENE FROM A GASEOUS ENVIRONMENT

(76) Inventor: Lawrence R. Sadler, Palmetto, FL (US)

(*) Notice: Subject to any disclaimer, the term of this patent is extended or adjusted under 35 U.S.C. 154(b) by 177 days.

This patent is subject to a terminal disclaimer.

(21) Appl. No.: 13/215,001

(22) Filed: Aug. 22, 2011

(65) Prior Publication Data

US 2011/0303087 A1  Dec. 15, 2011

Related U.S. Application Data (63) Continuation-in-part of application No. 11/635,150, filed on Dec. 7, 2006, now Pat. No. 8,002,877.

(51) Int. Cl.
*B01D 53/02* (2006.01)
*B01D 53/72* (2006.01)

(52) U.S. Cl.
USPC ............ 96/224; 96/134; 96/142; 96/154; 95/117; 95/144; 95/145; 95/148

(58) Field of Classification Search
USPC .............. 95/117, 144, 145, 148; 96/134, 96/142, 154, 224
See application file for complete search history.

(56) References Cited

U.S. PATENT DOCUMENTS

| | | |
|---|---|---|
| 1,909,811 A | 5/1933 | Connolly |
| 3,458,973 A | 8/1969 | Greathouse et al. |
| 3,958,028 A | 5/1976 | Burg |
| 4,061,483 A | 12/1977 | Burg |
| 4,818,602 A | 4/1989 | Yoshimi et al. |
| 6,071,472 A | 6/2000 | Caupin et al. |
| 6,358,374 B1 | 3/2002 | Obee et al. |
| 6,517,611 B1 | 2/2003 | Kuznicki et al. |
| 6,524,750 B1 | 2/2003 | Mansuetto |
| 6,641,788 B1 | 11/2003 | Ogawa et al. |
| 6,890,373 B2 | 5/2005 | Nemoto et al. |

(Continued)

FOREIGN PATENT DOCUMENTS

| | | |
|---|---|---|
| JP | 4187044 | 7/1992 |
| JP | 2002-204653 | 7/2002 |
| JP | 2004-337114 | 12/2004 |

OTHER PUBLICATIONS

Maneerat et al., "Photocatalytic Reaction of TiO2 to Decompose Ethylene in Fruit and Vegetable Storage", Transactions of the ASAE, 2003, vol. 46(3), pp. 725-730.

(Continued)

*Primary Examiner* — Christopher P Jones
(74) *Attorney, Agent, or Firm* — Kunzler Law Group (57) ABSTRACT

An apparatus, system, and method are disclosed for removing ethylene from a gaseous environment. Ethylene is a gaseous growth hormone produced by plants that triggers the ripening of some flowers, fruits, vegetables, and other plants. The apparatus includes an ethylene filter and a composition. The filter includes a frame and a trapping medium. The composition is attached to the trapping medium of the ethylene filter. The ethylene filter is positioned within a gaseous environment and is configured to encounter a gas flow within the gaseous environment. The composition contains at least some titanium dioxide which is configured to attach to the ethylene as the gas flow moves through and around the ethylene filter. In this manner, some ethylene may be removed from the gaseous environment.

20 Claims, 9 Drawing Sheets

(56) References Cited

U.S. PATENT DOCUMENTS

| | | | |
|---|---|---|---|
| 7,578,997 B2 * | 8/2009 | MacDonald | 424/76.1 |
| 8,182,800 B2 * | 5/2012 | MacDonald | 424/76.9 |
| 2003/0153457 A1 | 8/2003 | Nemoto et al. | |
| 2003/0203009 A1 * | 10/2003 | MacDonald | 424/443 |
| 2009/0104086 A1 | 4/2009 | Zax et al. | |

OTHER PUBLICATIONS

U.S. Appl. No. 12/800,521, Office Action dated Mar. 6, 2012.

* cited by examiner

FIG. 8 ent application of
and claims priority to U.S. patent application Ser. No. 11/635,
150 entitled "Method of Trapping Ethylene" and filed on Dec.
7, 2006, now U.S. Pat. No. 8,002,877 B1, for Lawrence
Sadler, which is incorporated herein by reference.

APPARATUS, SYSTEM, AND METHOD FOR REMOVING ETHYLENE FROM A GASEOUS ENVIRONMENT

CROSS-REFERENCES TO RELATED APPLICATIONS

This application is a continuation-in-part application of and claims priority to U.S. patent application Ser. No. 11/635,150 entitled "Method of Trapping Ethylene" and filed on Dec. 7, 2006, now U.S. Pat. No. 8,002,877 B1, for Lawrence Sadler, which is incorporated herein by reference.

FIELD

This invention relates to removing ethylene, a naturally occurring gaseous growth hormone produced by plant tissue, from a storage area and more particularly relates to removing ethylene from plant storage units to reduce ripening and unwanted maturing of the plant material stored in the storage unit.

BACKGROUND

Ethylene serves as a gaseous growth hormone for plants. It acts at trace levels throughout the life of the plant to stimulate or regulate the ripening of fruit, the opening of flowers, the shedding of leaves, and other plant functions. In particular, ethylene can stimulate fruit ripening in apples, induce pineapple flowing, hasten the coloring of harvested lemons, or inducing shedding of tree leaves prematurely. In many cases, ripening fruit and other plants produce large amounts of ethylene gas that can adversely affect plants surrounding the ripening fruit or plants. Ethylene has been identified as a natural product of not only fruits but of many other parts of plants, including leaves, stems, flowers, roots, tubers, and seedlings. The rate of ethylene production depends on both the type of plant tissue and its stage of development.

Premature ripening and degradation of plants caused by ethylene can interfere with productive use of those plants and is a major problem in the many industries involved in plant preservation. Ethylene can cause significant economic loss for florists, marketers, suppliers, shippers, and growers. In the field of produce transportation, for example, ripening can cause a decrease in shelf life of the transported produce resulting in a decrease in sales volume. In the field of cut flowers and potted plants, ethylene production can reduce shelf life and useful life after a sale. Studies have shown that removal of a portion of the ethylene from a gaseous environment can lower the spoilage rate of the plant materials In the cut flower industry a spoilage rate is associated with the amount of time that flowers can be used before spoilage. An average shelf life of ten to fourteen days, in refrigerated storage, exists prior to the commencement of deterioration beyond industry standards for retail sales. In addition to the shelf life before the retail sale, cut flowers must not deteriorate for a certain amount of time after the retail sale. Typically, industry standards require that the flowers not deteriorate for at least five days after the retail sale. Deterioration of cut flowers is judged by the more delicate outer leaves which are first to deteriorate. As a result, a reduction in the amount of ethylene that comes in contact with cut flowers is of utmost importance to the cut flower industry.

A need exists to extend the useful life of plant materials like cut flowers by removing ethylene from storage containers. Also, in the industry of organic foods, the spoilage rate tends to be more rapid due to the lack of food preservatives. Nothing can be added to organic foods or plants to prevent rapid ripening because such additives are not permitted to organic foods. A large need exists in the organic food industry to reduce the amount of ethylene that comes in contact with organic foods without adding to or altering the organic foods.

Problems can arise when ethylene producing commodities and ethylene sensitive commodities are transported or stored together. For example, high ethylene producers (such as ripe bananas, apples, and cantaloupe) can induce physiological disorders and/or undesirable changes in color, flavor, and texture in ethylene sensitive commodities (such as lettuce, cucumbers, carrots, potatoes, and sweet potatoes). Thus in the industry of food transportation, there exists a strong need to reduce the amount of ethylene that remains near transported foods. Due to the spoilage rate in each of the above mentioned industries and many more industries, there exists a very strong need to increase the shelf life period of the various plant materials by reducing the amount of ethylene that comes into contact with the plant materials.

A need also exists for a method of removing ethylene from a storage environment that is not based on breaking down the ethylene into carbon dioxide and water. Breaking down ethylene into carbon dioxide and water has major drawbacks. For example, breaking down ethylene into carbon dioxide and water requires expensive equipment with a high cost of installation. Additionally, there is a high cost of operating such systems due to energy needs and repair costs. A need exists for an inexpensive method that is not based on breaking down the ethylene but rather traps ethylene so that it can be removed from the gaseous environment.

SUMMARY

From the foregoing discussion, it should be apparent that a need exists for an apparatus, system, and method that can remove ethylene from a gaseous environment. Beneficially, such an apparatus, system, and method would remove ethylene from the gaseous environment without adding chemicals to the food or plants and would trap ethylene in order to remove it from a gaseous environment.

The present invention has been developed in response to the present state of the art, and in particular, in response to the problems and needs in the art that have not yet been fully solved by currently available food transportation and storage methods. Accordingly, the present invention has been developed to provide an apparatus, system, and method for removing ethylene from a gaseous environment that overcome many or all of the above-discussed shortcomings in the art.

The apparatus to remove ethylene from a gaseous environment is provided with a plurality of parts configured to functionally execute the necessary steps of removing ethylene from the gaseous environment. These parts in the described embodiments include an ethylene filter and a composition.

The apparatus, in one embodiment, is configured to remove ethylene from a gaseous environment and contains an ethylene filter and a composition. In one embodiment, the ethylene filter includes a frame and a trapping medium. The frame, in one embodiment, encases an outer edge of the trapping medium. In another embodiment, the ethylene filter is positioned within a gaseous environment and configured to encounter a gas flow within the gaseous environment. In one embodiment, the gaseous environment includes at least some ethylene.

In a further embodiment, the composition is connected to the trapping medium of the ethylene filter. The composition may include at least some titanium dioxide. The composition is positioned, in one embodiment, on the trapping medium such that the composition encounters the gas flow within the gaseous environment. In one embodiment, the composition removes ethylene from the gas flow by allowing at least some portion of the ethylene to attach to the titanium dioxide of the composition.

In another embodiment, the apparatus includes an ultra violet light source ("UV light source") which is capable of producing light within the ultra violet spectrum. In another embodiment, the UV light source broadcasts at least a portion of the light produced by the UV light source onto the gas flow. The light produced by the UV light source, in one embodiment, is configured to render inert some bacteria, germs, and other airborne contaminants within the gas flow.

In a further embodiment, the apparatus also includes an air circulation means. In one embodiment, the UV light source includes a plurality of ultra-violet lamps which are positioned between the air circulation means and the ethylene filter. In one embodiment, the UV light source is positioned such that at least a portion of the light broadcasts on the ethylene filter and a portion of the light broadcasts on the gas flow.

In yet another embodiment, the apparatus includes a sodium silicate filter. In one embodiment, the sodium silicate filter includes a second frame and a second trapping medium where the second frame encases an outer edge of the second trapping medium. In an additional embodiment, at least some sodium silicate is attached to the second trapping medium. The second trapping medium, in one embodiment, is positioned within the gaseous environment and configured to encounter the gas flow within the gaseous environment. In one embodiment, the gaseous environment includes some ethylene and some moisture and the sodium silicate is configured to remove a portion of the moisture from the gas flow.

In a further embodiment, the sodium silicate filter and the ethylene filter are positioned such that the gas flow first encounters the sodium silicate filter and then encounters the ethylene filter. In another embodiment, the apparatus includes a UV light source which is positioned such that the gas flow first encounters the light from the UV light source and then encounters the sodium silicate filter and the ethylene filter, respectively.

In one embodiment, the composition includes at least some titanium dioxide and at least some sodium silicate. In yet another embodiment, the trapping medium includes a plurality of passageways. In one embodiment, the trapping medium is made of a substantially air impermeable substance such that the gas flow passes over surfaces of the passageways and through the passageways without passing through the substantially air impermeable substance of the trapping medium. In yet another embodiment, each passageway includes six sides and each of the six sides is equally shaped. In one embodiment, each passageway shares one side with each of the adjoining passageways.

A system of the present invention is also presented to remove ethylene from a gaseous environment. In particular, the system, in one embodiment, includes a casing, a gas circulation means, at least one gas flow director, an ethylene filter, a composition, and a light source.

In one embodiment, the casing is positioned within a gaseous environment. The system includes, in one embodiment, a gas circulation means which is attached to the casing. In one embodiment, the gas circulation means creates a gas flow within the gaseous environment and the casing. In another embodiment, a gas flow director is attached to the casing and directs the gas flow created by the gas circulation means.

In a further embodiment, an ethylene filter is attached to the casing. The ethylene filter may include a frame and a trapping medium which may be similar to the frame and trapping medium discussed above. In a further embodiment, the frame encases an outer edge of the trapping medium. In one embodiment, the ethylene filter is configured to encounter the gas flow within the gaseous environment. In another embodiment, a composition, containing at least some titanium dioxide, is connected to the trapping medium of the ethylene filter. In another embodiment, the composition is positioned on the trapping medium such that the composition encounters the gas flow. In one embodiment, the composition removes ethylene from the gas flow by allowing at least some portion of the ethylene to attach to the titanium dioxide of the composition.

In a further embodiment, the system includes a light source attached to the casing. The light source is configured, in one embodiment, to render inert some germs, bacteria, and other airborne contaminants in the gas flow.

In another embodiment, the system includes a filter reconditioning unit. The filter reconditioning unit, in one embodiment, includes a filter reconditioning casing, a heat production means, a gas circulation means, and an exhaust. In one embodiment, the filter reconditioning unit is configured to receive an ethylene filter. In one embodiment, the gas circulation means and the heat production means create a heated gas flow which contacts the ethylene filter and removes the trapped ethylene from the ethylene filter. In one embodiment, the filter reconditioning unit then expels the ethylene through the exhaust.

In one embodiment, the light source of the system includes one of either a plurality of low intensity ultra violet light producing elements or a plurality of LED light producing elements. In another embodiment, the gas circulation means produces a gas flow which is directed by the gas flow director at the light from the light source and at the ethylene filter. In another embodiment, the light source functions when the gas circulation means is operating.

In one embodiment, the composition includes substantially equal portions of titanium dioxide and sodium silicate. In another embodiment the composition containing titanium dioxide and the sodium silicate is mixed prior to application to the filter. In yet another embodiment, the ethylene filter comprises a plurality of layers and each layer is connected to an amount of the composition.

A method of the present invention is also presented for removing ethylene from a gaseous environment. The method in the disclosed embodiments substantially includes the steps necessary to carry out the functions presented above with respect to the operation of the described apparatus and system. In one embodiment, the method includes providing an ethylene filter with a frame and a trapping medium. In one embodiment, the frame encases an outer edge of the trapping medium. The method also may include placing the ethylene filter in a gaseous environment which includes at least some ethylene and some moisture, and positioning the ethylene filter within the gaseous environment such that the ethylene filter encounters a gas flow within the gaseous environment.

The method may also include providing a composition and connecting the composition to the trapping medium of the ethylene filter. In one embodiment, the composition includes at least titanium dioxide and sodium silicate. The composition, in one embodiment, is positioned on the trapping medium such that the composition encounters the gas flow within the gaseous environment. In another embodiment, the composition removes ethylene and moisture from the gas flow by allowing at least some portion of the ethylene to attach to the titanium dioxide of the composition and allowing a portion of the moisture to attach to the sodium silicate of the composition.

The method may also include creating a gas flow within the gaseous environment such that at least a portion of the gas flow encounters the trapping medium. In another embodiment, the method includes removing the ethylene filter from the gaseous environment and removing trapped ethylene and moisture from the ethylene filter by applying heated air to the ethylene filter. In a further embodiment, the trapping medium includes at least a first layer and a second layer and the composition is applied on an inside surface of the first and second layers.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of filters, ultra violet light sources, fans, casings, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
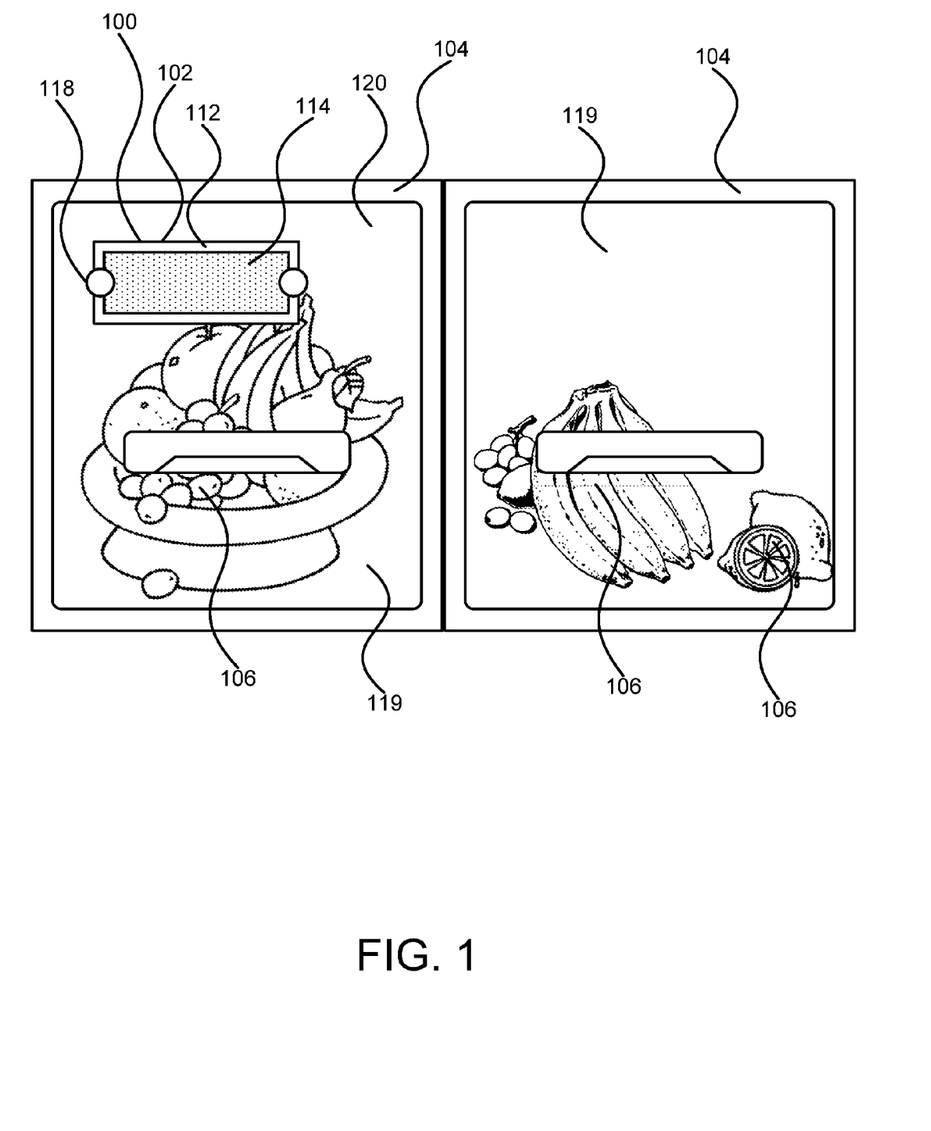
FIG. 1 is a perspective view illustrating one embodiment of an apparatus for removing ethylene from a gaseous environment in accordance with the present invention.
Figure 2:
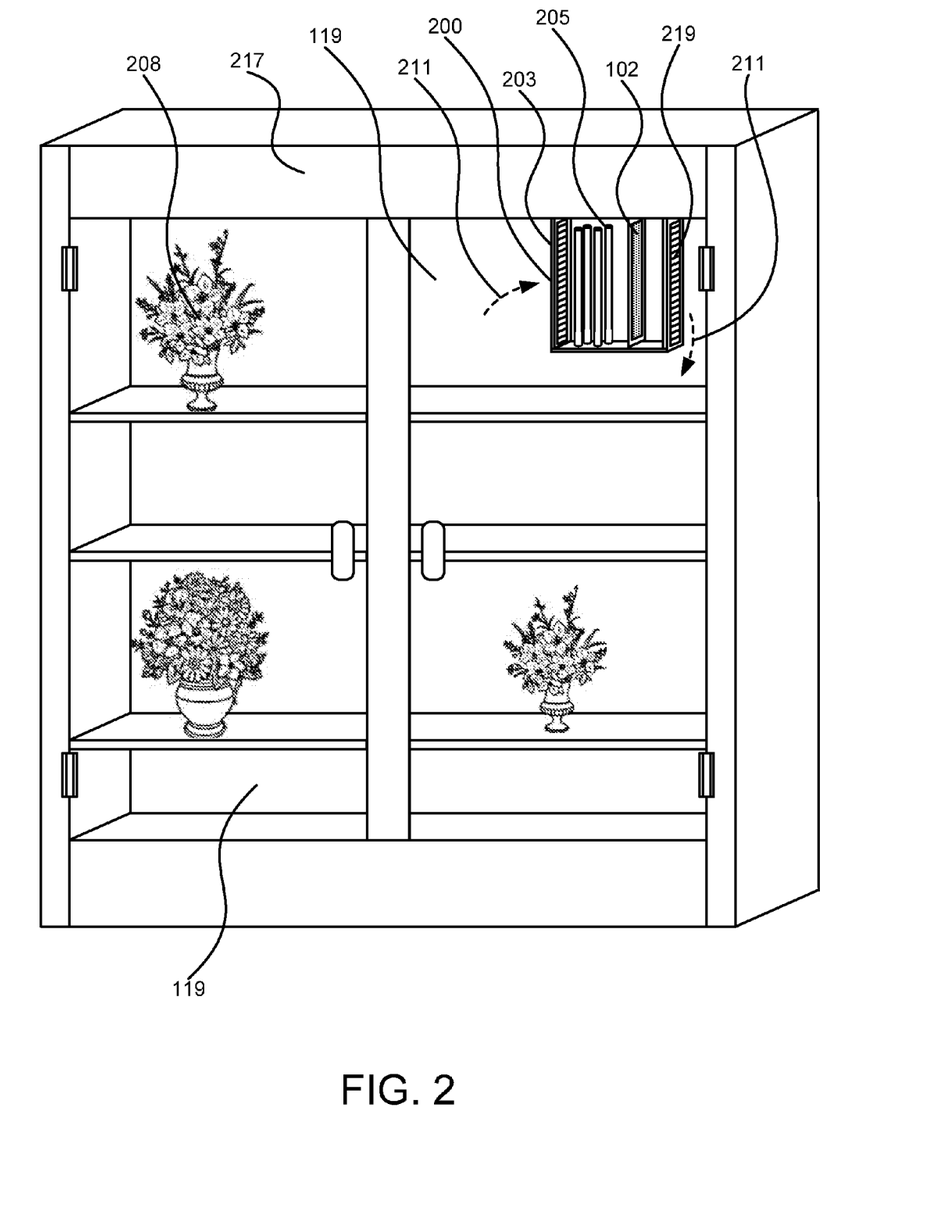
FIG. 2 is a perspective view illustrating another embodiment of an apparatus for removing ethylene from a gaseous environment in accordance with the present invention.

FIG. 1 depicts one embodiment of an apparatus 100 to remove ethylene from a gaseous environment 119. The illustrated apparatus 100 includes an ethylene filter 102 and a composition. Generally, the composition is attached to the ethylene filter 102 and the ethylene filter 102 is placed in a gaseous environment 119. In one embodiment, the gaseous environment 119 contains gas, at least some of which is ethylene. Examples of gaseous environments 119 that may contain ethylene include produce transportation vehicles, sea/land cargo containers, airplane container transportation units, plant storage refrigerators 217, grocery store storage containers, refrigerator vegetable bins 104, and the like. Ethylene is produced by many plants and acts as a ripening agent for those and other plants. In the embodiment of FIG. 1, the ethylene within the gaseous environment 119 is produced by food material 106. In the embodiment of FIG. 2, the ethylene within the gaseous environment 119 is produced by cut flowers 208 in a flower arrangement. The composition that is attached to the ethylene filter 102, in one embodiment, contains at least some titanium dioxide which attaches to some of the ethylene as the ethylene moves past the ethylene filter 102. In one embodiment, the gas within the gaseous environment 119 moves within the gaseous environment 119 by way of a gas flow 211. In one embodiment, the gas flow 211 passes through and around the ethylene filter 102 and ethylene attaches to the composition. In this manner, ethylene is removed from the gas flow 211. In one embodiment, the ethylene filter 102 can then be removed from the gaseous environment 119 so that the trapped ethylene can be released from the ethylene filter 102 outside of the gaseous environment 119. In another embodiment, the ethylene filter 102 can be removed from the gaseous environment 119 and simply thrown away.

In the embodiment of FIG. 1, the ethylene filter 102 is placed within a common vegetable bin 104 in a common refrigerator. In this embodiment, the vegetable bin 104 contains ethylene due to the presence of food material 106 within the vegetable bin 104. In the embodiment of FIG. 1, the ethylene filter 102 is attached to a clear face 120 of the vegetable bin 104 through the use of suction cups 118. One of skill in the art will recognize that there are many other methods and means for attaching the ethylene filter 102 to a surface of the vegetable bin 104 of FIG. 1, such as an adhesive, mounting slots, screws, etc. The ethylene filter 102 is positioned to encounter a gas flow 211 within the gaseous environment 119. In one embodiment, the ethylene filter 102 is attached to the clear face 120 of the vegetable bin 104 so that an amount of space remains between the clear face 120 and the ethylene filter 102 such that the gas flow 211 came move through and around the ethylene filter 102.

In one embodiment, the gas flow 211 within the gaseous environment 119 is created by a gas circulation means 601, such as a fan. In another embodiment, the gas flow 211 is created by movement of an open air, partially-covered produce transportation vehicle or by an air duct in a covered produce transportation vehicle. In yet another embodiment, the gas flow 211 is created by an air conditioning unit in a produce transportation vehicle or a produce storage unit. In this embodiment, the ethylene filter 102 may be placed within ducts for the air conditioning unit or within the storage unit itself. In another embodiment, the air conditioning unit may contain an air filter 315 and the ethylene filter 102 is installed behind the air filter 315. In the embodiment of FIG. 1, the gas flow 211 is created by opening and closing the vegetable bin 104. In another embodiment, the gas flow 211 is created by opening and closing a door in a refrigerator or produce transportation vehicle. In one embodiment, the gas flow 211 moves within the gaseous environment 119 and at least a portion of the gas flow 211 encounters the ethylene filter 102 and the composition.

In one embodiment, the ethylene filter 102 contains a frame 112 and a trapping medium 114. In one embodiment, the frame 112 encases the outer edge of the trapping medium 114, as shown in FIG. 1. The frame 112 and corresponding trapping medium 114 may be in any shape. In the embodiment of FIG. 1, the frame 112 and trapping medium 114 are rectangular in shape. The frame 112 may also be made from a plurality of different materials and mixtures of materials. In one embodiment, the frame 112 is made of a paper material. In another embodiment, the frame 112 is made of a plastic material that is water-impervious or water-resistant. In one embodiment, for example, the frame 112 is made of a polyurethane mixture. In another embodiment, the frame 112 is made of a rubber material. In yet another embodiment, the frame 112 is made of a foam material. The frame 112 may be rigid or flexible depending on the material used to construct the frame 112. The frame 112 may be disposable or may be reusable such that a new trapping medium 114 can be placed within a reusable frame 112.

Figure 6:
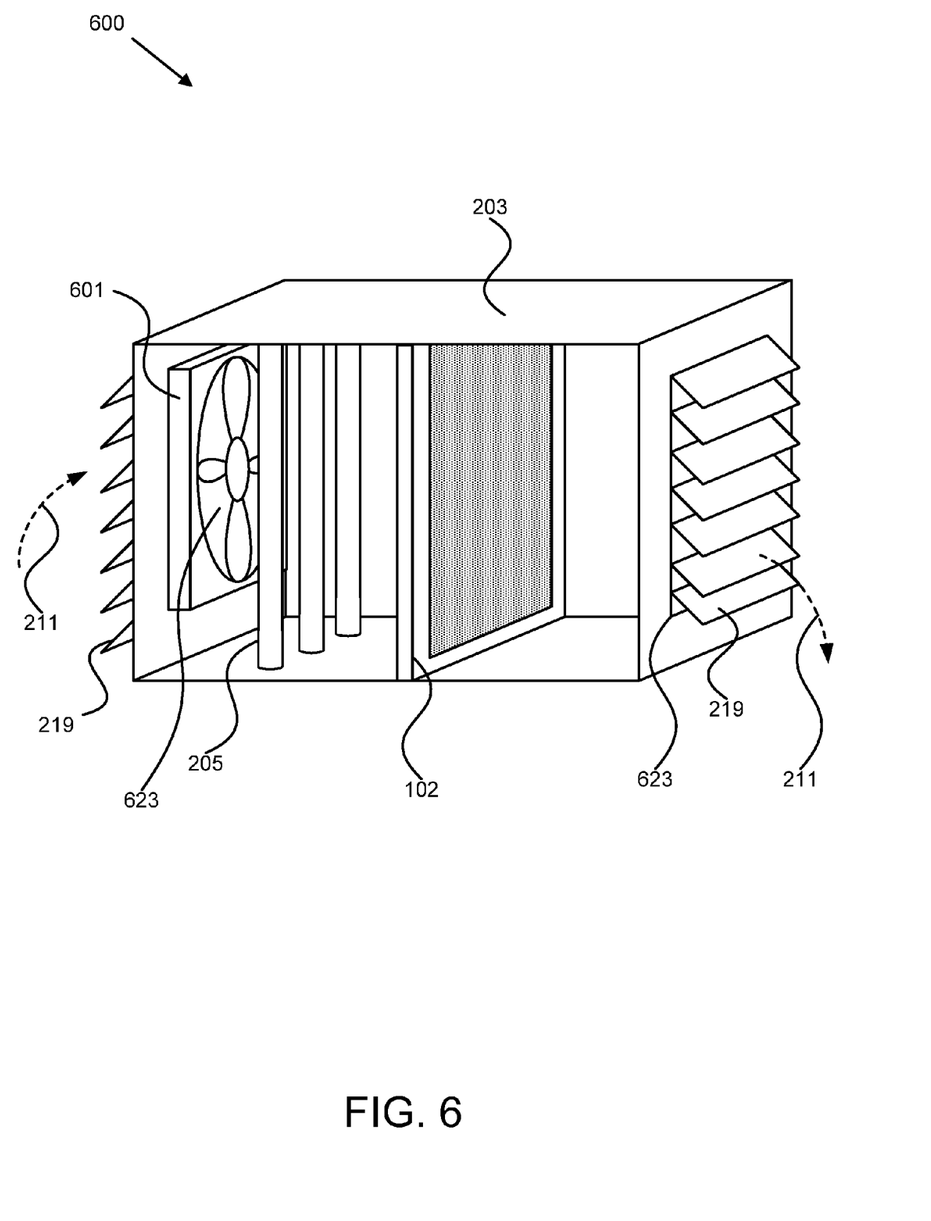
FIG. 6 is a cutaway perspective side view illustrating another embodiment of an apparatus for removing ethylene from a gaseous environment in accordance with the present invention.

In the embodiment of FIG. 1, the ethylene filter 102 is attached to a clear face 120 of the vegetable bin 104 through the use of suction cups 118. In another embodiment, the frame 112 is placed in a slot that corresponds to the frame 112. In the embodiment of FIG. 2, the frame 112 is placed in a casing 203. In another embodiment, the frame 112 is simply placed on a shelf in a refrigeration unit. In the embodiment of FIG. 6, the frame 112 is located in a casing 203. In one embodiment, the frame 112 contains a stand and the stand holds the frame 112 upright in the gaseous environment 119.

Figure 5:
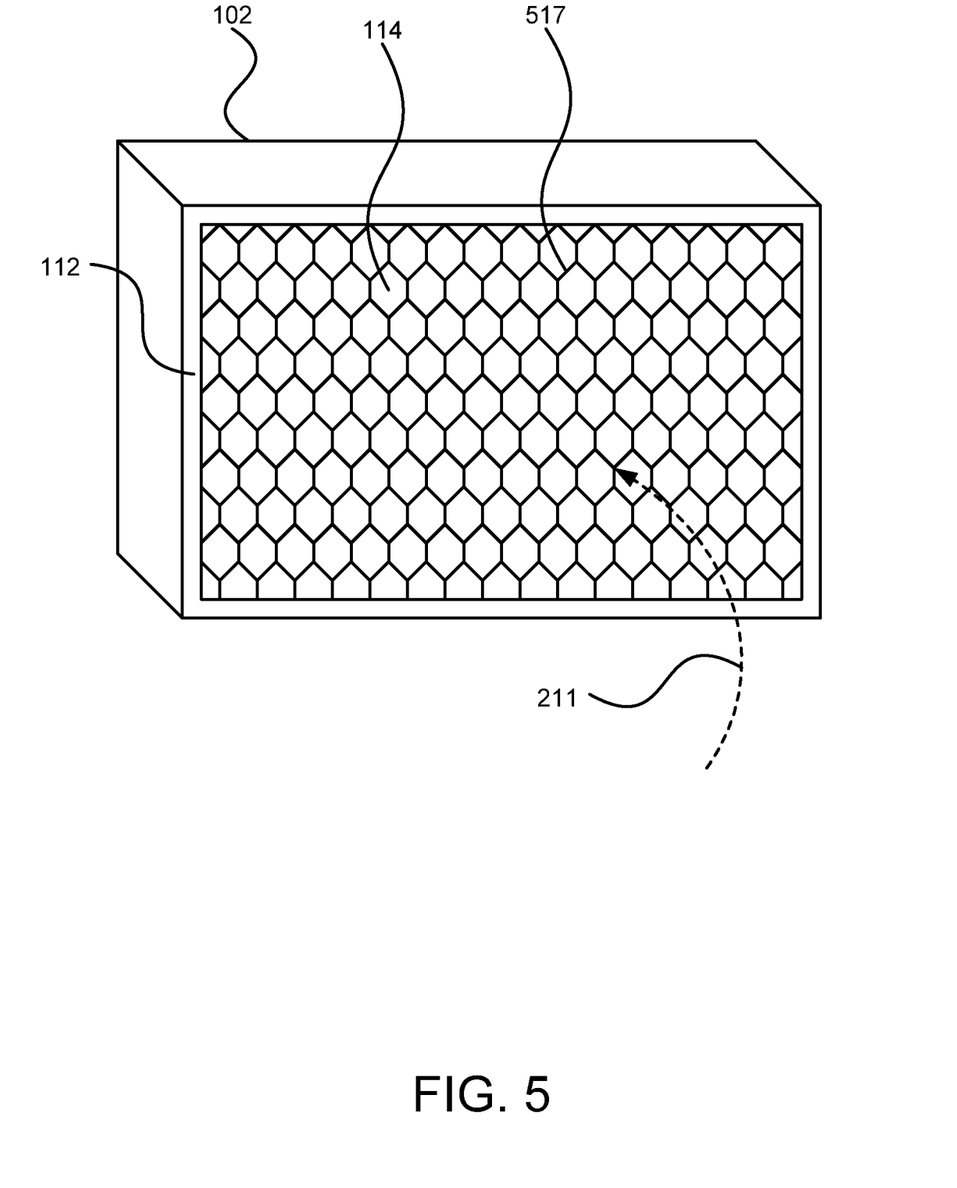
FIG. 5 is a perspective view illustrating one embodiment of an ethylene filter in accordance with the present invention.

In one embodiment, the trapping medium 114 is made of a typical air filter material. In one embodiment, the air filter material is made of pleated, layered paper. In another embodiment, the air filter material is a spun fiberglass material. In another embodiment, the air filter material comprises a fibrous material through which air can pass. Other example embodiments of the trapping medium 114 include fiberglass pre-filter material, pleated pre-filter material, 3-ply graduated density media pre-filter material, and other types of filter material. In one embodiment, the trapping medium 114 is made of a pleated material. In another embodiment, the trapping medium 114 is a honeycomb-shaped material, as shown in FIG. 5. In another embodiment, the trapping medium 114 is made of a very large quantity of fiberglass strands in an overlying pattern.

In one embodiment, the trapping medium 114 is made of large pore paper which allows at least some solid particles in the air, such as dust, pollen, mold and bacteria, to pass through the trapping medium 114 without clogging the trapping medium 114. In one embodiment, the trapping medium 114 is a filtering material that allows most airborne contaminants to pass through while providing a substantial surface area which is contacted by the passing gas flow 211. In yet another embodiment, the trapping medium 114 is made of a spun fiberglass material. In yet another embodiment, the trapping medium 114 is made of a foam material.

The composition is attached to the trapping medium 114. In one embodiment, the trapping medium 114 includes at least a first layer and a second layer. In this embodiment, the composition is applied on an inside surface of the first and second layers thus trapping the composition between the first and second layers and preventing the composition from moving outside of the first and second layers. In yet another embodiment, the trapping medium 114 is collapsible for easy storage.

The composition, in one embodiment, contains at least some titanium dioxide and may contain other liquids or solids. In one embodiment, the composition contains titanium dioxide and purified water. In another embodiment, the composition contains titanium dioxide, purified water, and a bonding agent to help secure the composition to the trapping medium 114. In one embodiment, the composition is configured to remove ethylene from the gas flow 211 by allowing some of the ethylene from the gas flow 211 to attach to the titanium dioxide of the composition.

In one embodiment, the composition is positioned on the trapping medium 114 and then baked onto the trapping medium 114. In one embodiment, the composition is sprayed onto the trapping medium 114. In another embodiment, the trapping medium 114 is soaked in the composition and then the trapping medium 114 is allowed to dry. In one embodiment, the ethylene filter 102 contains a plurality of layers and each layer is coated in an amount of the composition. In one embodiment, the composition is a slurry which is created with purified water and titanium dioxide. This embodiment of the composition is applied to the trapping medium 114 and baked until dry to firmly attach the composition to the trapping medium 114.

In the embodiment of FIG. 1, the ethylene filter 102 has the composition attached thereon. The ethylene filter 102 is located within a gaseous environment 119 inside a typical vegetable bin 104. The ethylene filter 102 is spaced away from the clear face 120 of the vegetable bin 104 so that the gas flow 211 can pass through and around the ethylene filter 102. As the gas flow 211 passes through and around the ethylene filter 102, ethylene from the gas flow 211 attaches to the titanium dioxide and is removed from the gas flow 211. In this manner, the overall ethylene content of the gaseous environment 119 is lowered. In another embodiment, the titanium dioxide of the ethylene filter 102 also absorbs moisture from the gaseous environment 119. In this manner, both ethylene and moisture can be removed from the gaseous environment 119.

FIG. 2 depicts one embodiment of an apparatus 200 to remove ethylene from a gaseous environment 119 that may be similar to the apparatus 100 of FIG. 1. FIG. 2 shows a cutaway side view of the apparatus 200 so that an inner area of the apparatus 200 can be seen. The illustrated apparatus 200 includes an ethylene filter 102, a composition, two gas flow directors 219, and an ultra violet light source ("UV light source 205"). As described generally above, in one embodiment, the ethylene filter 102 is placed in a gaseous environment 119 that contains at least some ethylene. A composition containing at least some titanium dioxide is attached to the ethylene filter 102. A gas flow 211 within the gaseous environment 119 passes by and though the ethylene filter 102 and at least some of the ethylene in the gas flow 211 attaches to the titanium dioxide in the composition. In this manner, in one embodiment, ethylene is removed from the gaseous environment 119 and the overall ethylene content of the gaseous environment 119 is reduced. In one embodiment, the ethylene filter 102 can then be removed from the gaseous environment 119 so that the trapped ethylene can be released outside of the gaseous environment 119.

In one embodiment, the apparatus 200 includes a UV light source 205 which is capable of producing light within the ultra violet spectrum. In one embodiment, the UV light source 205 is configured to render inert some of the bacteria (for example, *aeromaonas hydrophila*, *campylobacter jejuni*, and *Escherichia coli*), viruses (for example, coxsackievirus, Hepatitus A, and Poliovicus Type 1), chlorine-resistant protozoa (such as *cryptosporidium* and *giardia*), and other airborne contaminants in the gas flow 211. The UV light source 205 can be located in different positions with regard to the ethylene filter 102. In one embodiment, the UV light source 205 is placed before the ethylene filter 102 so that the gas flow 211 first encounters the light from the UV light source 205 and then encounters the ethylene filter 102, as shown in FIG. 2. In another embodiment, the UV light source 205 is placed after the ethylene filter 102 so that the gas flow 211 encounters the ethylene filter 102 and then encounters the light from the UV light source 205. In yet another embodiment, there are multiple UV light sources 205 and multiple ethylene filters 102 that are oriented in an alternating pattern. In one embodiment, the UV light source 205 broadcasts at least some light onto the ethylene filter 102. In another embodiment, the UV light source 205 does not broadcast light onto the ethylene filter 102.

There are many different types of UV light sources 205 that can produce UV light and that may be part of the apparatus 200. In one example embodiment, the UV light source 205 is a lamp or series of lamps. In the embodiment of FIG. 2, the UV light source 205 is a series of four UV lamps. In other example embodiments, the UV light source 205 is a cold cathode germicidal UV lamp, a hot cathode germicidal UV lamp, a slimline germicidal UV lamp, and a high output germicidal UV lamp. In another embodiment, the UV light source 205 is a single ultraviolet lamp or bulb. In one embodiment, the UV light source 205 is a mercury-vapor lamp designed to produce ultraviolet radiation. In another embodiment, the UV light source 205 is a fluorescent lamp that produces ultraviolet light. In one embodiment, the UV light source 205 is a lamp that produces light with wavelengths from 280 to 320 nm. In one embodiment, the UV light source 205 is a photochemical lamp designed to destroy mold particles. In yet another embodiment, the UV light source 205 is a lamp that produces light with wavelengths from 220 to 280 nm. In yet another embodiment, the UV light source 205 is a germicidal lamp used to reduce airborne bacteria and to kill certain airborne organisms. In other embodiments, the UV light source 205 may be any other type of UV source that produces light in the ultraviolet spectrum and can direct that light onto the gas glow.

In one embodiment, the apparatus 200 includes a gas circulation means 601, as shown in FIG. 6. In one embodiment, the UV light source 205 is positioned between the gas circulation means 601 and the ethylene filter 102, as shown in FIG. 6. In one embodiment, the UV light source 205 includes a plurality of ultraviolet lamps which are positioned between the air circulation means and the ethylene filter 102. In one embodiment, the UV light source 205 is positioned such that at least a portion of the light broadcasts on the ethylene filter 102 and a portion of the light broadcasts on the gas flow 211. In this manner, the UV light source 205 renders inert certain germs, bacteria, and other contaminants in the gas flow 211 and on the ethylene filter 102.

In one embodiment, the apparatus 200 is configured to be situated in an upper area of a plant storage refrigerator 217, as shown in FIG. 2. Ethylene is slightly lighter than air and therefore higher concentrations of ethylene are found in the upper area of storage areas such as the plant storage refrigerator 217 of FIG. 2.

Figure 3:
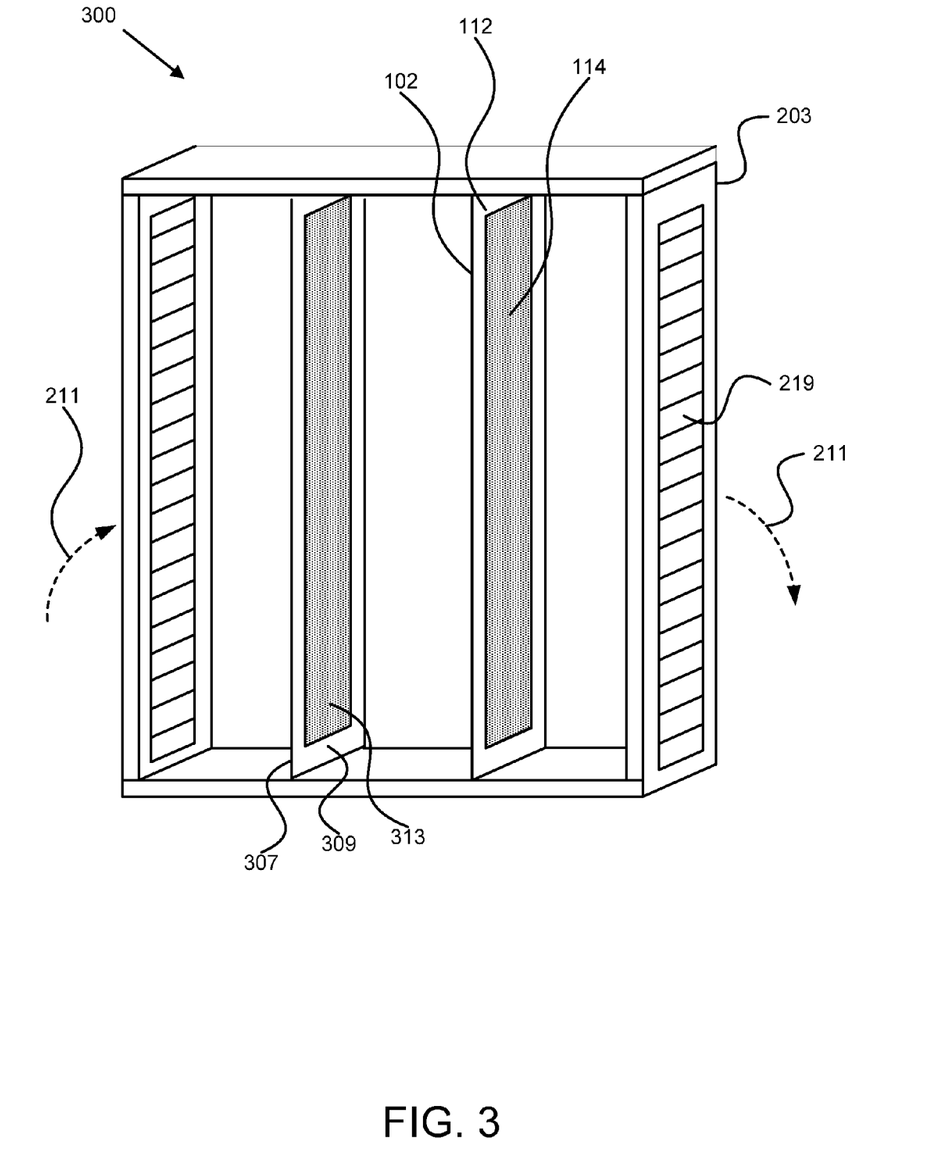
FIG. 3 is a cutaway perspective side view illustrating another embodiment of an apparatus for removing ethylene from a gaseous environment in accordance with the present invention.

FIG. 3 depicts one embodiment of an apparatus 300 to remove ethylene from a gaseous environment 119 that may be similar to the apparatus 100 of FIG. 1. FIG. 3 shows a cutaway side view of the apparatus 300 so that the inside of the apparatus 300 can be seen. The illustrated apparatus 300 includes an ethylene filter 102 which includes a frame 112 and a trapping medium 114, a composition, and a sodium silicate filter 307. As described generally above, in one embodiment, the ethylene filter 102 is placed in a gaseous environment 119 that contains at least ethylene. A composition which contains at least some titanium dioxide is attached to the ethylene filter 102. The titanium dioxide attaches to at least some of the ethylene as the ethylene moves past the ethylene filter 102 in a gas flow 211. In one embodiment, the ethylene filter 102 can then be removed from the gaseous environment 119 so that the trapped ethylene can be released outside of the gaseous environment 119. In this manner, ethylene is removed from the gaseous environment 119.

In one embodiment, the apparatus 300 includes a sodium silicate filter 307 in addition to the ethylene filter 102. In one embodiment, the sodium silicate filter 307 contains a second frame 309 and a second trapping medium 313. In one embodiment, the second frame 309 and the second trapping medium 313 are similar to the frame 112 and trapping medium 114 associated with the ethylene filter 102. In one embodiment, the second frame 309 encases an outer edge of the second trapping medium 313.

In one embodiment, at least some sodium silicate is attached to the sodium silicate filter 307. In one embodiment, the sodium silicate is in a silica gel form and is applied to the surface of the sodium silicate filter 307. The sodium silicate filter 307 may be placed within the gaseous environment 119 and is configured to encounter the gas flow 211 within the gaseous environment 119. In certain embodiments, the gaseous environment 119 may contain moisture. The moisture may, in some cases, create growing conditions for unwanted bacteria and mold. In one embodiment, the sodium silicate filter 307 removes a portion of the moisture from the gas flow 211 as the gas flow 211 passes around and through the sodium silicate filter 307, thereby reducing the likelihood that mold will form within the gaseous environment 119. In one embodiment, the sodium silicate filter 307 removes moisture from the gas flow 211 by allowing the sodium silicate to absorb moisture from the gas flow 211.

In one embodiment, the sodium silicate filter 307 and the ethylene filter 102 are configured such that the gas flow 211 first encounters the sodium silicate filter 307 and then encounters the ethylene filter 102. In one embodiment, the sodium silicate on the sodium silicate filter 307 acts to remove moisture from the gas flow 211 before the moisture reaches the titanium dioxide on the ethylene filter 102. In another embodiment, the sodium silicate filter 307 and the ethylene filter 102 are configured such that the gas flow 211 first encounters the ethylene filter 102 and then encounters the sodium silicate filter 307. In yet another embodiment, the sodium silicate filter 307 and the ethylene filter 102 are placed side-by-side such that the gas flow 211 encounters both filters simultaneously.

In one embodiment, sodium silicate is sprayed onto the sodium silicate filter 307. In another embodiment, the sodium silicate filter 307 is manually coated in sodium silicate. In another embodiment, the sodium silicate is mixed with a liquid to create a sodium silicate mixture and then sodium silicate filter 307 is immersed in the sodium silicate mixture. In one embodiment, the sodium silicate filter 307 is baked to secure the sodium silicate to the sodium silicate filter 307.

In another embodiment, the apparatus 300 contains only an ethylene filter 102 and the composition contains both titanium dioxide and sodium silicate. In one embodiment, the sodium silicate is added to the composition before the composition is applied to the ethylene filter 102. Thus the composition contains at least some titanium dioxide and some sodium silicate. In one embodiment, the composition contains almost equal portions of titanium dioxide and sodium silicate. In another embodiment, the sodium silicate is applied to the ethylene filter 102 after the composition has been applied to the ethylene filter 102. In one embodiment, the ethylene filter 102 is coated in the composition and then coated in sodium silicate.

Figure 3A:
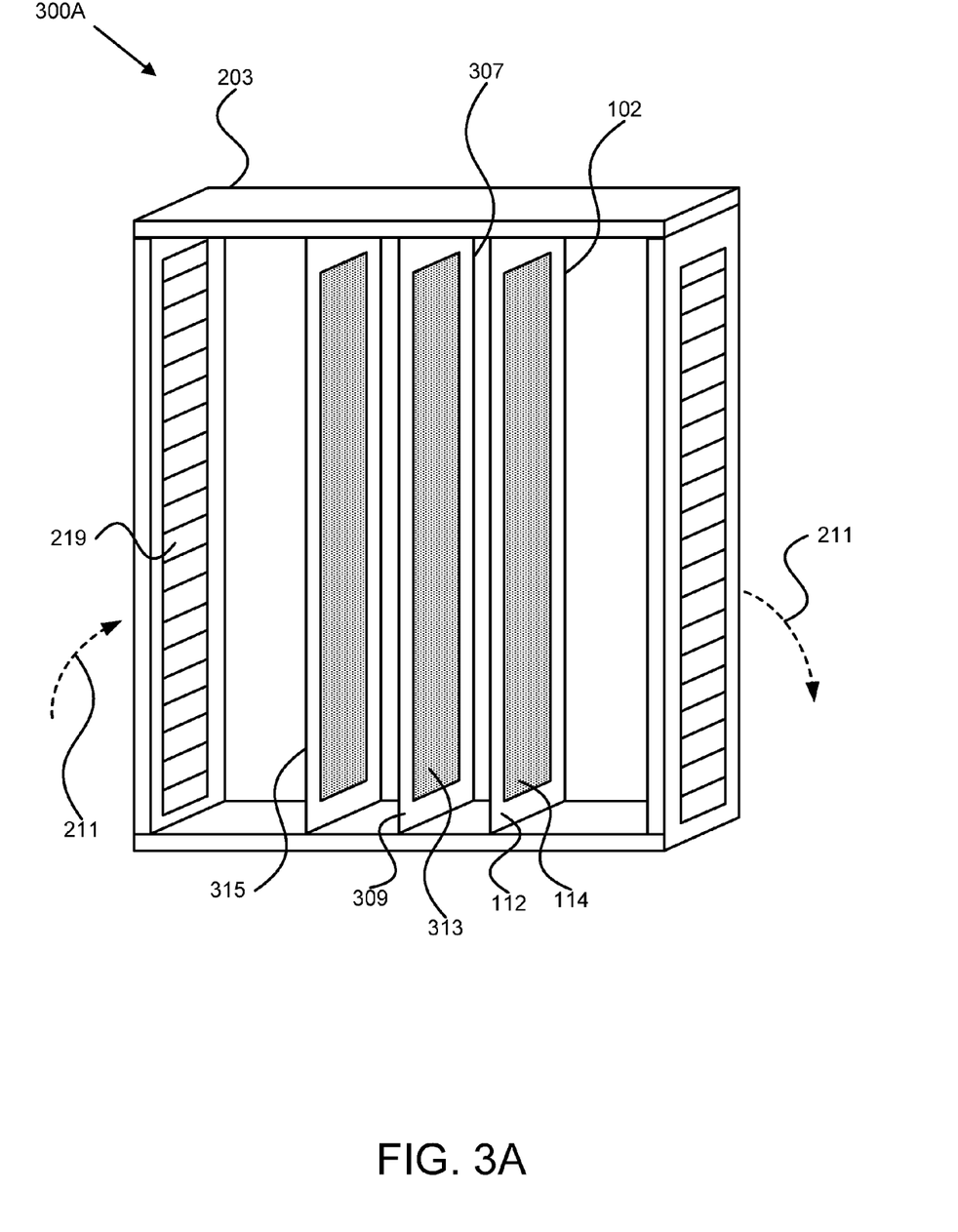
FIG. 3A is a cutaway perspective side view illustrating another embodiment of an apparatus for removing ethylene from a gaseous environment in accordance with the present invention.

In the embodiment of FIG. 3A, the apparatus 300A includes an air filter 315 positioned before the ethylene filter 102 such that the gas flow 211 first encounters the air filter 315 and then encounters the ethylene filter 102. In one embodiment, the air filter 315 cleans the gas flow 211 of a portion of the airborne contaminants within the gas flow 211 before the gas flow 211 reaches the ethylene filter 102. The air filter 315 can be any type of typical air filter including but not limited to pre-filters, final filters, and HEPA filters.

In one embodiment, the frame 112 contains not only the trapping medium 114 but also the second trapping medium 313. In another embodiment, the frame 112 contains the trapping medium 114, the second trapping medium 313, and a typical air filter medium. In one embodiment, the trapping medium 114, the second trapping medium 313, and the typical air filter medium are layered within the frame 112 such that the gas flow 211 passes through each medium as it passes through the frame 112.

Figure 4:
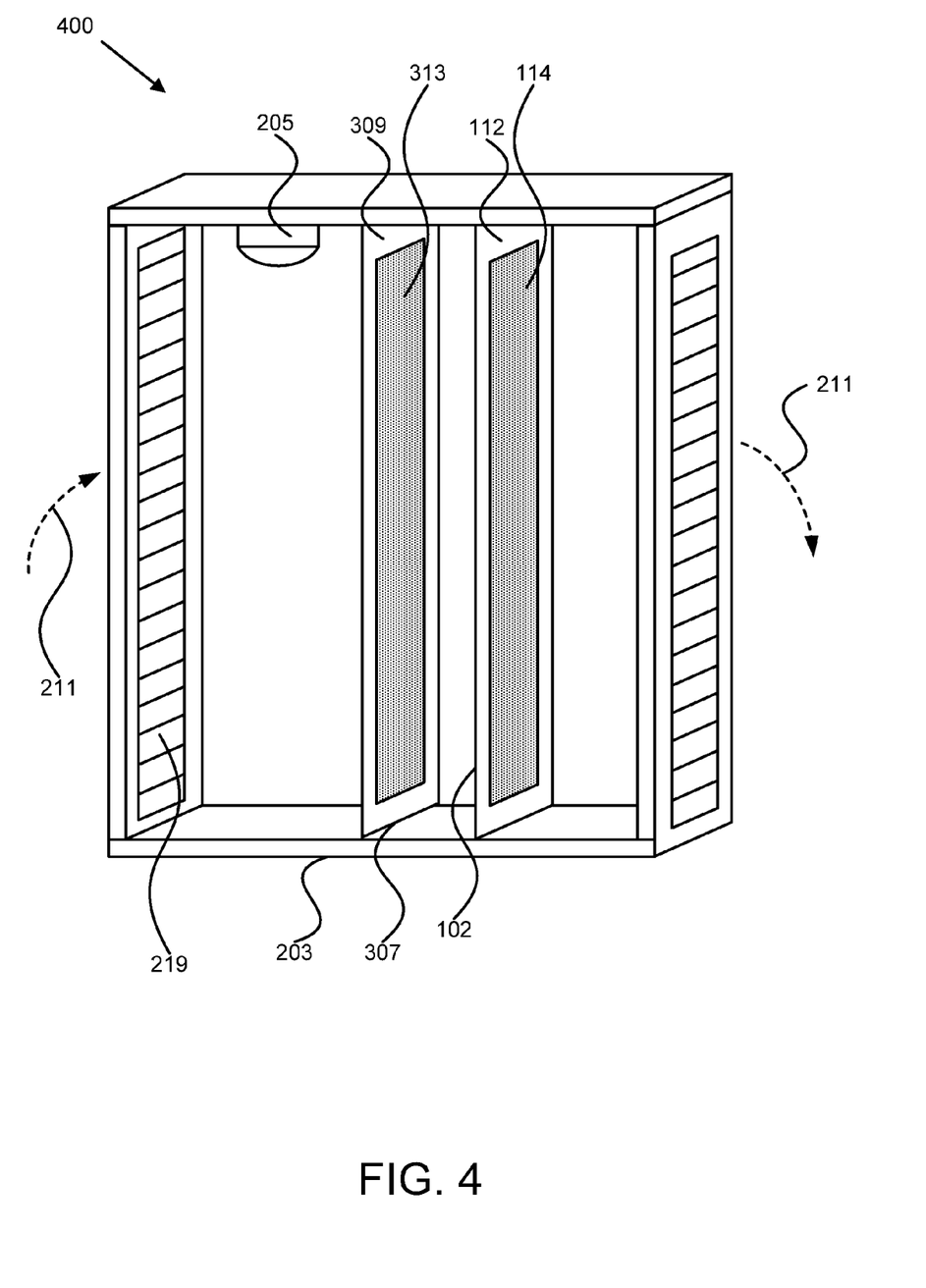
FIG. 4 is a cutaway perspective side view illustrating another embodiment of an apparatus for removing ethylene from a gaseous environment in accordance with the present invention.

FIG. 4 depicts one embodiment of an apparatus 400 to remove ethylene from a gaseous environment 119 that may be similar to the apparatus 100 of FIG. 1. The illustrated apparatus 400 includes an ethylene filter 102, a composition, a sodium silicate filter 307, and a UV light source 205. As described generally above, in one embodiment, the ethylene filter 102 and sodium silicate filter 307 are placed in a gaseous environment 119 that contains at least some ethylene. A composition containing titanium dioxide is attached to the ethylene filter 102. The titanium dioxide attaches to some of the ethylene as the ethylene moves past the ethylene filter 102 in the gas flow 211 within the gaseous environment 119, thus removing a portion of the ethylene from the gaseous environment 119. The apparatus 400 may also contain a sodium silicate filter 307. The sodium silicate is configured to encounter the gas flow 211 and to remove at least some moisture from the gas flow 211. In one embodiment, the apparatus 400 also includes a UV light source 205 that projects UV light onto the gas flow 211. The UV light source 205 is configured to render inert certain types and amounts of bacteria and other airborne contaminants.

In one embodiment, the apparatus 400 is configured as shown in FIG. 4. In the embodiment of FIG. 4, the UV light source 205 is configured such that the gas flow 211 first encounters the light from the UV light source 205 and then encounters the sodium silicate filter 307 and the ethylene filter 102, respectively. In another embodiment, the UV light source 205 is positioned between an air circulation means and the ethylene filter 102. In one embodiment, the UV light source 205 is positioned such that light from the UV light source 205 is partially broadcast onto the surface of the ethylene filter 102 or the sodium silicate filter 307. In one embodiment, two UV light sources 205 are included in the apparatus 400, one of which broadcasts light onto the ethylene filter 102 and one of which broadcasts light onto the sodium silicate filter 307. In another embodiment, the UV light source 205 broadcasts light onto multiple components of the apparatus 400 to render inert bacteria and mold on the surfaces of the multiple components. Any activation of the titanium dioxide caused by broadcasting light from the UV light source 205 onto the ethylene filter 102 is incidental and is not relied on to remove ethylene from the gaseous environment 119. In one embodiment, one UV light source 205 is positioned upstream from the ethylene filter 102 and a second UV light source 205 is positioned downstream from the ethylene filter 102. In one embodiment, the UV light source 205 produces light when the air circulation means is functioning.

FIG. 5 depicts one embodiment of an ethylene filter 102 that may be similar to the ethylene filter 102 of FIG. 1. The illustrated ethylene filter 102 includes a frame 112 and a trapping medium 114. As described generally above, in one embodiment, the ethylene filter 102 is placed in a gaseous environment 119 that contains at least ethylene and the ethylene filter 102 traps some of that ethylene through the use of the composition. The composition contains titanium dioxide which attaches to some of the ethylene in the gaseous environment 119.

In the embodiment of FIG. 5, the trapping medium 114 contains a plurality of passageways 517 running through the trapping medium 114. In another embodiment, the second trapping medium 313 also contains a plurality of passageways 517 running through the second trapping medium 313. In one embodiment, the passageways 517 touch each other and produce a surface through which gas can move. In one embodiment, the trapping medium 114 is made of air impermeable substance such that the gas flow 211 can pass over the surfaces of the trapping medium 114 but cannot pass through the substance of the trapping medium 114. In this embodiment, the composition is placed on surfaces of the trapping medium 114 and the composition contacts the gas flow 211 as the gas flow 211 flows over and through the plurality of passageways 517. In one embodiment, the passageways 517 are sufficiently large that most airborne particles, such as dust and mold, are not trapped in the trapping medium 114. In one embodiment, the passageways 517 are sufficiently open that UV light from the UV light source 205 can pass through the passageways 517.

In one embodiment, the passageways 517 each contain six sides, as shown in FIG. 5. In this embodiment, each of the six sides is equally shaped and each passageway 517 shares one side with each of the adjoining passageways 517. In one embodiment, the trapping medium passageways 517 are oriented in a honeycomb pattern, similar to that shown in FIG. 5. In one embodiment, the passageways 517 are 2 inches deep so that the surface area onto which the composition can be attached is large. In one embodiment, the passageways 517 are deeper than 2 inches to further increase the surface area onto which the composition may be attached. In another embodiment, the passageways 517 are less than 2 inches deep to allow the ethylene filter 102 to fit within a smaller area, such as a vegetable bin 104.

FIG. 6 depicts one embodiment of an apparatus 600 to remove ethylene from a gaseous environment 119 that may be similar to the apparatus 100 of FIG. 1. The illustrated apparatus 600 includes a casing 203, a gas circulation means 601, two gas flow directors 219, an ethylene filter 102, a composition, and a light source 721. As described generally above, in one embodiment, the ethylene filter 102 is placed in a gaseous environment 119 that contains at least ethylene. A composition containing at least some titanium dioxide is attached to the ethylene filter 102. The titanium dioxide attaches to some of the ethylene as the gas flow 211 moves past and through the ethylene filter 102.

In one embodiment, the apparatus 600 contains a casing 203 which is positioned within the gaseous environment 119. The casing 203 contains the ethylene filter 102, the gas circulation means 601, and the UV light source 205. In one embodiment, the casing 203 is a rectangular, metal structure. In another embodiment, the casing 203 is a plastic material. The embodiment of FIG. 6 shows a rectangular casing 203 with one wall removed so that the inside of the casing 203 can be seen. In one embodiment, the apparatus 600 contains multiple slots to accept different types and numbers of ethylene filters 102, sodium silicate filters 307, air filters 315, and other types of filters.

In the embodiment of FIG. 6, the casing 203 contains two openings 623 so that the gas flow 211 can enter one opening 623 and exit through the other opening 623. In one embodiment, the gas circulation means 601 is positioned next to one of the openings 623. In another embodiment, the casing 203 contains a plurality of openings 623 such that gas may flow in many directions through and around the casing 203.

In one embodiment, the apparatus 600 contains a gas circulation means 601 which is attached to the casing 203. In one embodiment, the gas circulation means 601 creates a gas flow 211 within the gaseous environment 119 and through the casing 203. In one embodiment, the gas circulation means 601 forces air into the casing 203 and through the trapping medium 114. In another embodiment, the gas circulation means 601 creates a suction force that pulls gas from the casing 203 into the gaseous environment 119. In one embodiment, the apparatus 600 includes two gas circulation means 601 where one gas circulation means 601 forces gas into the casing 203 while one gas circulation means 601 pulls gas from the casing 203.

Figure 7:
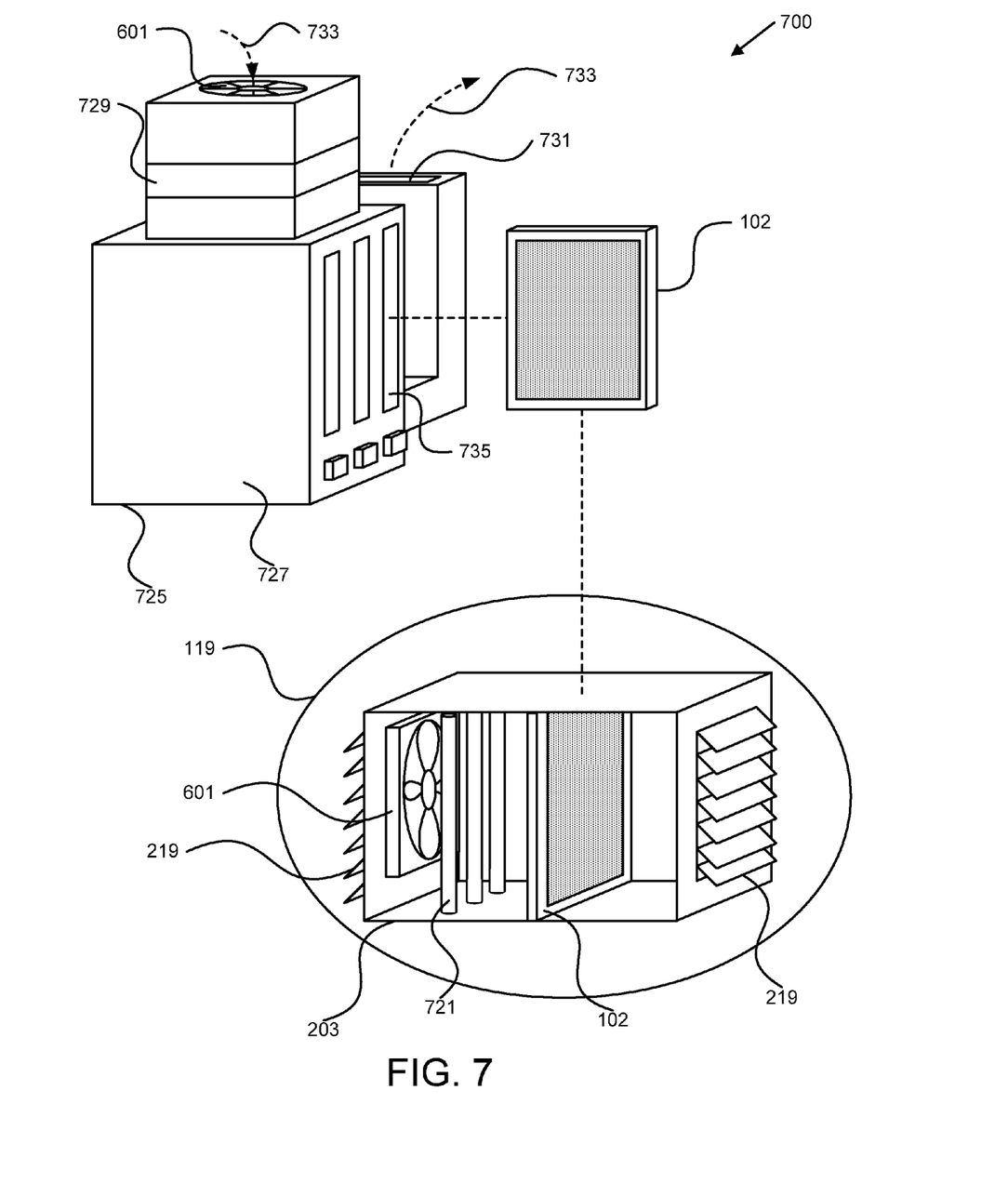
FIG. 7 is a perspective view illustrating one embodiment of a system for removing ethylene from a gaseous environment in accordance with the present invention.

In one embodiment, the gas circulation means 601 is a propeller fan, as shown in FIG. 7. In one embodiment, the gas circulation means 601 can be set to several different speed settings. In other embodiments, as explained above, the gas flow 211 is created by other means other than the gas circulation means 601.

In one embodiment, at least one gas flow director 219 is attached to the casing 203. The gas flow director 219 is configured to direct the gas flow 211 into and out of the casing 203. In the embodiment of FIG. 6, the gas flow 211 directors move the gas flow 211 in a circular direction, as shown by the gas flow arrows 211. In one embodiment, the gas flow directors 219 are louvers. In one embodiment, the gas flow directors 219 are angled downward and prevent moisture from dripping into the casing 203. In another embodiment, the gas flow director 219 directs the gas flow 211 at the light from the light source 721 and at the ethylene filter 102.

In one embodiment, the ethylene filter 102 is also attached to the casing 203. In the embodiment of FIG. 6, the frame 112 of the ethylene filter 102 contacts an interior surface of the casing 203 and is held to the casing 203. In one embodiment, the composition is positioned on the trapping medium 114 so that the gas flow 211 encounters the composition as it passes through the casing 203. As stated above, the composition removes ethylene from the gas flow 211 by allowing at least some portion of the ethylene to attach to the titanium dioxide of the composition.

FIG. 7 depicts one embodiment of a system 700 to remove ethylene from a gaseous environment 119 that may be similar to the apparatus 100 of FIG. 1. The illustrated system 700 includes a casing 203, a gas circulation means 601, two gas flow directors 219, an ethylene filter 102, a composition, a light source 721, and a filter reconditioning unit 725. As described generally above, in one embodiment, the ethylene filter 102 is placed in a gaseous environment 119 that contains at least ethylene. A composition is attached to the ethylene filter 102. The composition contains at least some titanium dioxide which attaches to some of the ethylene as the ethylene moves past the ethylene filter 102 in a gas flow 211. In one embodiment, the ethylene filter 102 can then be removed from the gaseous environment 119 so that the trapped ethylene can be released outside of the gaseous environment 119. In this manner, ethylene is removed from the gaseous environment 119.

In one embodiment, the system 700 contains a filter reconditioning unit 725 which receives the ethylene filter 102 when it is removed from the casing 203 and the gaseous environment 119. In one embodiment, the filter reconditioning unit 725 contains a filter reconditioning casing 727, a heat production means 729, a gas circulation means 601, and an exhaust 731.

In one embodiment, the filter reconditioning unit 725 is configured to receive the ethylene filter 102 within the filter reconditioning casing 727. The gas circulation means 601 and the heat production means 729, in one embodiment, create a heated gas flow 733 which contacts the ethylene filter 102. In one embodiment, the heated gas flow 733 is configured to remove the trapped ethylene from the ethylene filter 102 and expel the ethylene through the exhaust 731. In this manner, the ethylene is removed from the ethylene filter 102 so that that ethylene filter 102 can be reused to collect ethylene from the gaseous environment 119. In one embodiment, the heat of the heated gas flow 733 also releases any moisture collected by either the ethylene filter 102 or the sodium silicate filter 307. As stated above, any activation of the titanium dioxide by the heat of the heated gas flow 733 is incidental and not relied on to convert ethylene to carbon dioxide and water. In one embodiment, the gas circulation means 601 moves the heated gas flow 733 through the ethylene filter 102 in a direction opposite to that of the gas flow 211 when the ethylene filter 102 was in the gaseous environment 119.

In one embodiment, the ethylene filter 102 can be reused multiple times. In one embodiment, the filter reconditioning unit 725 contains a plurality of slots 735 to receive a plurality of ethylene filters 102. In this embodiment, a plurality of ethylene filters 102 can be reconditioned simultaneously.

In one embodiment, the heat production means 729 is a natural gas heater. In another embodiment, the heat production means 729 is a propane heater. In yet another embodiment, the heat production means 729 is an electric heater. In another embodiment, the heat production means 729 is a heat pump.

In one embodiment, the system 700 contains a light source 721 which is attached to the casing 203. The light source 721, in one embodiment, may be different than the UV light source 205 described above. For example, in one embodiment, the light source 721 is an LED light producing element that is configured to render inert certain types of bacteria and other airborne contaminants. In another embodiment, the light source 721 consists of a plurality of individual low intensity, ultra violet light producing elements. In one embodiment, the light source 721 is the same as the UV light source 205 discussed above.

In the embodiment of FIG. 7, the light source 721 is positioned between the gas circulation means 601 and the ethylene filter 102. In another embodiment, the light source 721 is positioned such that the ethylene filter 102 is between the gas circulation means 601 and the light source 721. In one embodiment, the light source 721 is a series of individual light sources 721, as shown in FIG. 7. In yet another embodiment, the light source 721 functions when the gas circulation means 601 is operating.

In one embodiment, the filter reconditioning unit 725 contains a gas circulation means 601 which is configured to create a gas flow 211 through the filter reconditioning casing 727. In one embodiment, the gas circulation means 601 circulates air through the ethylene filter 102 during reconditioning. The gas circulation means 601 used in the filter reconditioning unit 725 may be similar to the gas circulation means 601 used in the apparatus 600. In one embodiment, the filter reconditioning unit 725 contains an exhaust 731 configured to discharge the released ethylene from the filter reconditioning unit 725. In another embodiment, the exhaust 731 is also used to expel moisture released from the ethylene filter 102 and the sodium silicate filter 307.

Figure 8:
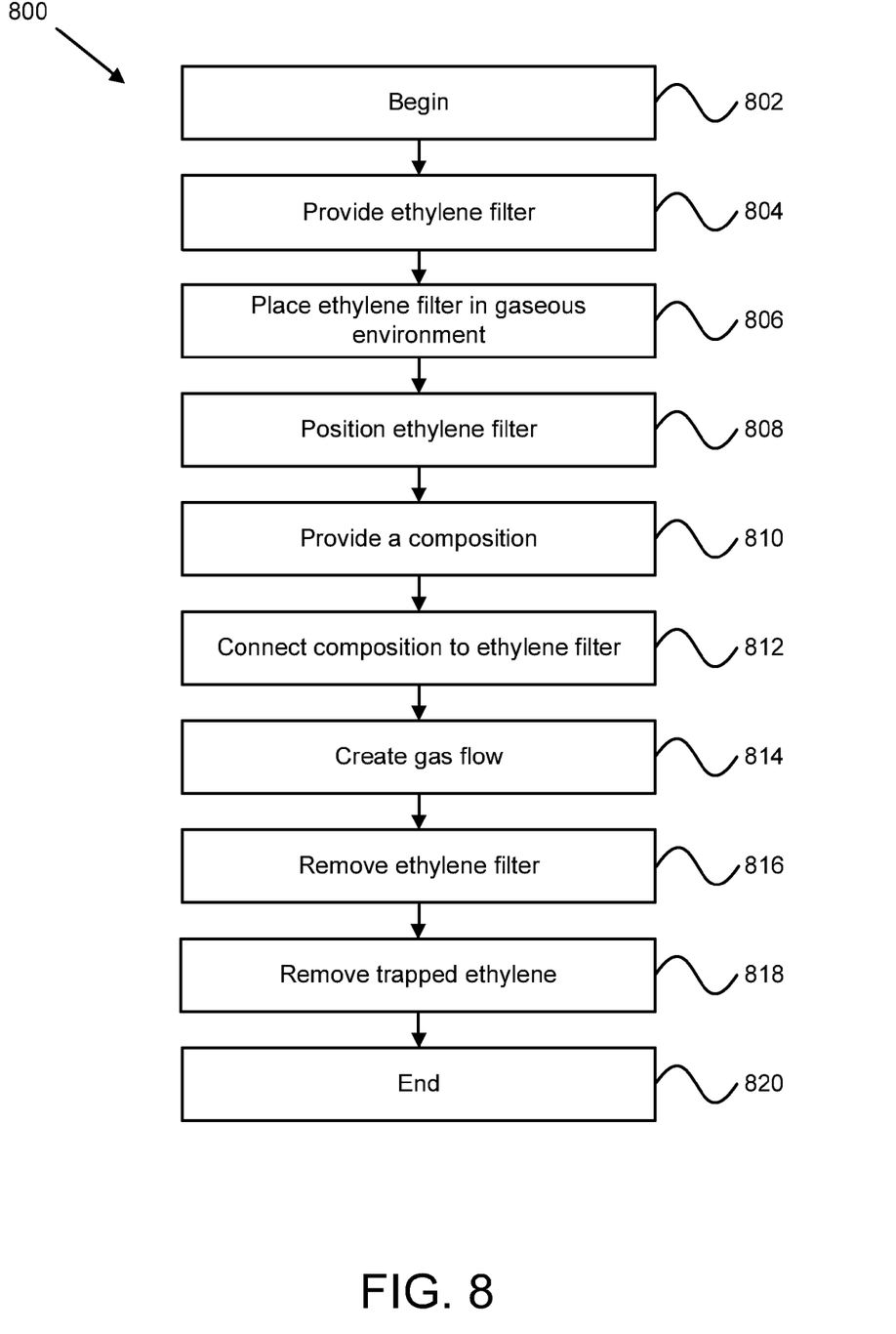
FIG. 8 is a schematic block diagram illustrating one embodiment of a method for removing ethylene from a gaseous environment in accordance with the present invention.

FIG. 8 depicts one embodiment of a method 800 for removing ethylene from a gaseous environment 119. In the illustrated method 800, the method 800 begins 802 and an ethylene filter 102 is provided 804. In one embodiment, the ethylene filter 102 contains a frame 112 and a trapping medium 114. In an additional embodiment, the frame 112 encases an outer edge of the trapping medium 114. In one embodiment, the ethylene filter 102 is placed 806 in a gaseous environment 119 which comprises at least ethylene and moisture. In one embodiment, the ethylene filter 102 is positioned 808 within the gaseous environment 119 such that the ethylene filter 102 encounters a gas flow 211 within the gaseous environment 119.

The method 800, in one embodiment, also includes providing 810 a composition and connecting 812 the composition to the trapping medium 114 of the ethylene filter 102. In one embodiment, the composition contains titanium dioxide and sodium silicate. In another embodiment, the composition is positioned on the trapping medium 114 such that the composition encounters the gas flow 211 within the gaseous environment 119. In this manner, the composition removes ethylene and moisture from the gas flow 211 by allowing at least some portion of the ethylene to attach to the titanium dioxide and allowing a portion of the moisture to attach to the sodium silicate.

In another embodiment, the method 800 includes creating 814 a gas flow 211 within the gaseous environment 119. In one embodiment, at least a portion of the gas flow 211 encounters the trapping medium 114. In yet another embodiment, the method 800 includes removing 816 the ethylene filter 102 from the gaseous environment 119 and removing 818 trapped ethylene and moisture from the ethylene filter 102 by applying heated air to the ethylene filter 102. The method then ends 820.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising: a container containing a gaseous environment, wherein the gaseous environment comprises at least ethylene; an ethylene filter comprising a frame and a trapping medium, the frame encasing an outer edge of the trapping medium, the ethylene filter positioned within the gaseous environment and configured to encounter a gas flow within the gaseous environment; and a composition connected to the trapping medium of the ethylene filter, the composition comprising at least titanium dioxide, the composition positioned on the trapping medium such that the composition encounters the gas flow within the gaseous environment, the composition further configured to remove ethylene from the gas flow by allowing at least some portion of the ethylene to attach to the titanium dioxide of the composition.

2. The apparatus of claim 1, further comprising an ultra violet light source ("UV light source") capable of producing light within the ultra violet spectrum, wherein the UV light source broadcasts at least a portion of the light produced by the UV light source onto the gas flow, wherein the light is configured to render inert some bacteria, germs, and other airborne contaminants within the gas flow.

3. The apparatus of claim 2, further comprising an air circulation means, wherein the UV light source comprises a plurality of ultra-violet lamps positioned between the air circulation means and the ethylene filter.

4. The apparatus of claim 2, wherein the UV light source is positioned such that at least a portion of the light broadcasts on the ethylene filter and a portion of the light broadcasts on the gas flow.

5. The apparatus of claim 1, further comprising a sodium silicate filter, wherein the sodium silicate filter comprises a second frame and a second trapping medium, the second frame encasing an outer edge of the second trapping medium, wherein at least some sodium silicate is attached to the second trapping medium, the second trapping medium positioned within the gaseous environment and configured to encounter the gas flow within the gaseous environment, wherein the gaseous environment comprises at least some ethylene and some moisture, wherein the sodium silicate is configured to remove a portion of the moisture from the gas flow.

6. The apparatus of claim 5, wherein sodium silicate filter and the ethylene filter are positioned such that the gas flow first encounters the sodium silicate filter and then encounters the ethylene filter.

7. The apparatus of claim 6, further comprising a UV light source, wherein the UV light source is positioned such that the gas flow first encounters the light from the UV light source and then encounters the sodium silicate filter and the ethylene filter, respectively.

8. The apparatus of claim 1, wherein the composition comprises at least some titanium dioxide and at least some sodium silicate.

9. The apparatus of claim 1, wherein the trapping medium comprises a plurality of passageways, wherein the trapping medium comprises a substantially air impermeable substance such that the gas flow passes over surfaces of the passageways and through the passageways without passing through the substantially air impermeable substance of the trapping medium.

10. The apparatus of claim 9, wherein each passageway comprises six sides, wherein each of the six sides is equally shaped and each passageway shares one side with each of the adjoining passageways.

11. A system to comprising: a casing containing a gaseous environment, wherein the gaseous environment comprises at least ethylene; an gas circulation means attached to the casing, wherein the gas circulation means is configured to create a gas flow within the gaseous environment and the casing; at least one gas flow director attached to the casing, the gas flow director configured to direct the gas flow created by the gas circulation means; an ethylene filter attached to the casing, the ethylene filter comprising a frame and a trapping medium, the frame encasing an outer edge of the trapping medium, the ethylene filter configured to encounter the gas flow; a composition connected to the trapping medium of the ethylene filter, the composition comprising at least titanium dioxide, the composition positioned on the trapping medium such that the composition encounters the gas flow, the composition further configured to remove ethylene from the gas flow by allowing at least some portion of the ethylene to attach to the titanium dioxide of the composition; and a light source attached to the casing, the light source configured to render inert some germs, bacteria, and other airborne contaminants in and around the gas flow.

12. The system of claim 11, further comprising a filter reconditioning unit, wherein the filter reconditioning unit comprises a filter reconditioning casing, a heat production means, a gas circulation means, and an exhaust, wherein the filter reconditioning unit is configured to receive the ethylene filter, wherein the gas circulation means and the heat production means create a heated gas flow which contacts the ethylene filter, wherein the heated gas flow is configured to remove the trapped ethylene from the ethylene filter and expel the ethylene through the exhaust.

13. The system of claim 11, wherein the light source comprises one of a plurality of low intensity ultra violet light producing elements and a plurality of LED light producing elements.

14. The system of claim 11, wherein gas circulation means produces a gas flow which is directed by the gas flow director, wherein the gas flow director directs the gas flow at the light from the light source and at the ethylene filter.

15. The system of claim 11, wherein the light source functions when the gas circulation means is operating.

16. The system of claim 11, wherein the composition comprises substantially equal portions of titanium dioxide and sodium silicate.

17. The system of claim 16, wherein the composition containing titanium dioxide and the sodium silicate is mixed prior to application to the filter.

18. The system of claim 11, wherein the ethylene filter comprises a plurality of layers, wherein each layer is connected to an amount of the composition.

19. A method for removing ethylene from a gaseous environment, the method comprising:
providing an ethylene filter, wherein the ethylene filter comprises a frame and a trapping medium, the frame encasing an outer edge of the trapping medium;
placing the ethylene filter in a gaseous environment which comprises at least ethylene and moisture and positioning the ethylene filter within the gaseous environment such that the ethylene filter encounters a gas flow within the gaseous environment;
providing a composition and connecting the composition to the trapping medium of the ethylene filter, the composition comprising at least titanium dioxide and sodium silicate, the composition positioned on the trapping medium such that the composition encounters the gas flow within the gaseous environment, the composition further configured to remove ethylene and moisture from the gas flow by allowing at least some portion of the ethylene to attach to the titanium dioxide of the composition and allowing a portion of the moisture to attach to the sodium silicate of the composition;
creating the gas flow within the gaseous environment, wherein at least a portion of the gas flow encounters the trapping medium;
removing the ethylene filter from the gaseous environment; and
removing trapped ethylene and moisture from the ethylene filter by applying heated air to the ethylene filter.

20. The method of claim 19, wherein the trapping medium comprises at least a first layer and a second layer, wherein the composition is applied on an inside surface of the first and second layers.

* * * * *